(12) United States Patent
Jaax et al.

(10) Patent No.: US 9,144,673 B2
(45) Date of Patent: **\*Sep. 29, 2015**

(54) SELF ANCHORING LEAD

(71) Applicant: BOSTON SCIENTIFIC NEUROMODULATION CORPORATION, Valencia, CA (US)

(72) Inventors: Kristen N. Jaax, Santa Clarita, CA (US); Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 349 days.

This patent is subject to a terminal disclaimer.

(21) Appl. No.: 13/709,959

(22) Filed: Dec. 10, 2012

(65) Prior Publication Data

US 2013/0123867 A1 May 16, 2013

Related U.S. Application Data

(63) Continuation of application No. 12/027,170, filed on Feb. 6, 2008, now Pat. No. 8,332,043.

(60) Provisional application No. 60/888,479, filed on Feb. 6, 2007.

(51) Int. Cl.
*A61N 1/00* (2006.01)
*A61N 1/05* (2006.01)
(Continued)

(52) U.S. Cl.
CPC ............... *A61N 1/05* (2013.01); *A61N 1/0573* (2013.01); *A61N 1/372* (2013.01); *A61B 5/6839* (2013.01); *A61N 1/375* (2013.01)

(58) Field of Classification Search
CPC ........... A61N 1/00; A61N 1/05; A61N 1/372; A61N 1/375; A61N 1/02; A61N 1/04; A61N 1/18; A47G 29/00; A47G 29/22; A61B 5/6839
USPC .......................................... 607/126, 128, 130
See application file for complete search history.

(56) References Cited

U.S. PATENT DOCUMENTS

| 3,877,679 A | 4/1975 | Lowe |
| 4,378,023 A | 3/1983 | Trabucco |

(Continued)

FOREIGN PATENT DOCUMENTS

| WO | WO-9640363 A1 | 12/1996 |
| WO | WO-9837926 A1 | 9/1998 |

(Continued)

OTHER PUBLICATIONS

Alo, Kenneth M. et al., "New Trends in Neuromodulation for the Management of Neuropathic Pain," Neurosurgery, Apr. 2002, 50(4):690-704.

(Continued)

*Primary Examiner* — Christopher D Koharski
*Assistant Examiner* — Elizabeth K So
(74) *Attorney, Agent, or Firm* — Lowe Graham Jones PLLC; Bruce E. Black

(57) ABSTRACT

An implantable device includes an electrode lead body and at least one stimulating electrode contact disposed on or within the electrode lead body, the lead body being configured and arranged to be self anchoring within body tissue. In addition, the invention is directed to methods of making and using such self anchoring implantable devices.

20 Claims, 4 Drawing Sheets

(51) Int. Cl.
*A61N 1/372* (2006.01)
*A61B 5/00* (2006.01)
*A61N 1/375* (2006.01)

(56) References Cited

U.S. PATENT DOCUMENTS

| | | | |
|---|---|---|---|
| 4,858,623 | A | 8/1989 | Bradshaw et al. |
| 5,193,539 | A | 3/1993 | Schulman et al. |
| 5,193,540 | A | 3/1993 | Schulman et al. |
| 5,312,439 | A | 5/1994 | Loeb |
| 5,545,207 | A | 8/1996 | Smits et al. |
| 5,571,162 | A | 11/1996 | Lin |
| 5,807,399 | A | 9/1998 | Laske et al. |
| 5,843,146 | A | 12/1998 | Cross, Jr. |
| 5,860,629 | A | 1/1999 | Reed |
| 5,871,532 | A | 2/1999 | Schroeppel |
| 6,051,017 | A | 4/2000 | Loeb et al. |
| 6,516,227 | B1 | 2/2003 | Meadows et al. |
| 6,609,029 | B1 | 8/2003 | Mann et al. |
| 6,741,892 | B1 | 5/2004 | Meadows et al. |
| 7,033,326 | B1 | 4/2006 | Pianca et al. |
| 7,231,260 | B2 | 6/2007 | Wallace et al. |
| 7,330,756 | B2 | 2/2008 | Marnfeldt |
| 7,460,913 | B2 | 12/2008 | Kuzma et al. |
| 7,596,414 | B2 | 9/2009 | Whitehurst et al. |
| 7,672,734 | B2 | 3/2010 | Anderson et al. |
| 7,706,892 | B2 | 4/2010 | Colvin et al. |
| 7,761,165 | B1 | 7/2010 | He et al. |
| 7,783,359 | B2 | 8/2010 | Meadows |
| 7,809,446 | B2 | 10/2010 | Meadows |
| 7,840,279 | B2 | 11/2010 | He |
| 7,953,498 | B1 | 5/2011 | Carbunaru et al. |
| 7,974,706 | B2 | 7/2011 | Moffitt et al. |
| 8,271,094 | B1 | 9/2012 | Moffitt et al. |
| 8,332,043 | B1 * | 12/2012 | Jaax et al. ............. 607/116 |
| 2004/0059392 | A1 | 3/2004 | Parramon et al. |
| 2005/0251239 | A1 | 11/2005 | Wallace et al. |
| 2006/0009827 | A1 | 1/2006 | Kurth et al. |
| 2006/0247749 | A1 | 11/2006 | Colvin |
| 2007/0150036 | A1 | 6/2007 | Anderson |
| 2007/0288077 | A1 | 12/2007 | Bulkes et al. |

FOREIGN PATENT DOCUMENTS

| | | |
|---|---|---|
| WO | WO-9843700 A1 | 10/1998 |
| WO | WO-9843701 A1 | 10/1998 |

OTHER PUBLICATIONS

Dodick, David W., "Occipital Nerve Stimulation for Chronic Cluster Headache," Advanced Studies in Medicine, 2003, 3(6C):S569-S571.

Kapural, Leonardo et al., "Occipital Nerve and Electrical Stimulation Via the Midine Approach and Subcutaneous Surgical Leads for Treatment of Severe Occipital Neuralgia: A Pilot Study," Anesthesia & Analgesia, 2005, 101:171-174

Matharu Manjit S. et al., "Central Neuromodulation in Chronic Migraine Patients With Suboccipital Stimulators: A PET study," Brain, 2004, 127(1):220-230.

Oh, Michael et al., "Minimally Invasive Peripheral Nerve Stimulation for the Treatment of Occipital Neuralgia," Pain Section Newsletter, Oct. 1999, pp. 3-5.

Oh, Michael Y. et al., "Peripheral Nerve Stimulation for the Treatment of Occipital Neuralgia and Transformed Migraine Using A C1-2-3 Subcutaneous Paddle Style Electrode: A Technical Report," Neuromodulation, 2004, 7(2):103-112.

Picaza, J. A. et al., "Pain Suppression by Peripheral Nerve Stimulation: Part II. Observations With Implanted Devices," Surgical Neurology, Jul. 1975, 4:115-126.

Picaza J. A. et al., "Pain Supression: Chronic Effects," Nuerosurgery, 1977, 1(2):226-227.

Picaza, J. A., "Pain Supression by Peripheral Nerve Stimulation: Chronic Effects of Implanted Devices," Applied Nuerophysiology, 1977/78, 40:223-234.

Popeney, Charles A. et al., "Peripheral Neurostimulation for the Treatment of Chronic, Disabling Transformed Migraine," Headache, Apr. 2003, 43:369-375.

Slavin, Konstantin V. et al, "Use of Long-term Nerve Stimulation With Implanted Electrodes in the Treatment of Intractable Craniofacial Pain," Pain Section Newsletter: Selected Abstracts; Annual AANS Meeting San Francisco 2000, Sep. 2000, p. 7.

Waisbrod, H. et al., "Direct Nerve Stimulation for Painful Peripheral Neuropathies," The Journal of Bone and Joint Surgery, May 1985, 67-B(3):470-472.

Weiner, Richard L. et al., "Peripheral Nerve Stimulation in the Treatment of Occipital Neuralgia," 4th International Congress of the International Neuromodulation Society; Joint Meeting with International Functional Electrical Stimulation Society, Sep. 16-20, 1998 Lucerne, Switzerland, XVIII. 2 (p. 108).

Weiner, Richard L. et al., "Peripheral Neurostimulation for Control of Intractable Occipital Neuralgia," Neuromodulation, 1999, 2(3):217-221.

Weiner, Richard L. et al., "Subcutaneous Neurostimulation for Intractable C2 Mediated Headaches," Pain Section Newsletter: Selected Abstracts; Annual AANS Meeting Toronto 2001, Fall 2001, p. 3.

U.S. Appl. No. 11/237,159, filed Sep. 28, 2005.
U.S. Appl. No. 60/888,479, filed Feb. 6, 2007.
U.S. Appl. No. 12/027,170, filed Feb. 6, 2008.
U.S. Appl. No. 12/027,170, Official Communication mailed May 25, 2011.
U.S. Appl. No. 12/027,170, Official Communication mailed Nov. 18, 2011.
U.S. Appl. No. 12/027,170, Official Communication mailed Feb. 16, 2012.

* cited by examiner

SELF ANCHORING LEAD

RELATED APPLICATIONS

This application is a continuation of U.S. patent application Ser. No. 12/027,170 filed Feb. 6, 2008, which claims the benefit of U.S. Provisional Patent Application Ser. No. 60/888,479, filed Feb. 6, 2007, all of which are herein incorporated by reference.

TECHNICAL FIELD

The invention is generally directed to implantable leads, and more particularly, but not exclusively, to implantable leads configured and arranged to be self anchoring within body tissue.

BACKGROUND

Implantable electrical stimulation devices have proven therapeutic in a variety of diseases and disorders. For example, pacemakers and implantable cardiac defibrillators have proven effective in the treatment of cardiac conditions. Spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

One disadvantage of these devices is that the electrode lead may migrate within the body. Migration may result in failure of the therapy or cause unwanted side effects. For example, some nerves are located next to or within muscles that may cause movement of the lead or catheter. Actuation of limbs may exert unequal pressures which can also cause migration.

The problem of migration may be particularly severe in cases of leads having a single electrode contact. Once the electrode contact has migrated away from its intended location in close proximity to its nerve target, the patient may have to use much higher electrical stimulation amplitudes to stimulate the nerve. In so doing, the patient may over stimulate the nerve endings resulting in pain and possibly even unwanted contraction of underlying muscle. In addition to these undesirable effects, the increased distance between the electrode contact and the nerve target may also result in an increase in the frequency the patient may have to charge the stimulation device to meet the energy demands of the higher amplitudes. This combination of side effects, painful skin over stimulation, undesirable muscle spasms, and/or frequent charging of the stimulation device may result in disuse of the therapy by the patient. Therefore, it is with respect to these considerations and others that the present invention has been made.

BRIEF SUMMARY

Embodiments of an implantable device are described that is configured and arranged to be self anchoring within body tissue, in addition, embodiments of methods of making and using such self anchoring implantable devices are described.

One embodiment is an implantable device having a body, a lead connector, and an anchoring portion on the body. The lead connector is coupled to the body off-center from a pivot point of the body. The anchoring portion is configured and arranged such that when the lead connector is employed to rotate the body about the pivot point, the anchoring portion of the body enables anchoring of the implantable device to a patient's body tissue when implanted.

Another embodiment is an implantable device for use in stimulating body tissue. The implantable device includes a body having at least one stimulating electrode contact disposed on the body, a lead connector coupled to the at least one stimulating electrode contact, and at least one anchoring member coupled to the body. The at least one anchoring member is configured and arranged such that when a force is applied through the lead connector, the body is rotated about a pivot point of the body, such that the at least one anchoring member facilitates anchoring of the implantable device within body tissue when implanted in the body tissue.

Yet another embodiment is a method for positioning an implantable device into body tissue. The method includes inserting an electrode lead body into body tissue. The electrode lead body includes at least one anchoring member configured and arranged on the electrode lead body, and a lead connector coupled to the electrode lead body off center from a pivot point on the electrode lead body. The method further includes employing the lead connector to rotate the electrode lead body about the pivot point such that the at least one anchoring member enables anchoring of the implantable device to surrounding body tissue.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
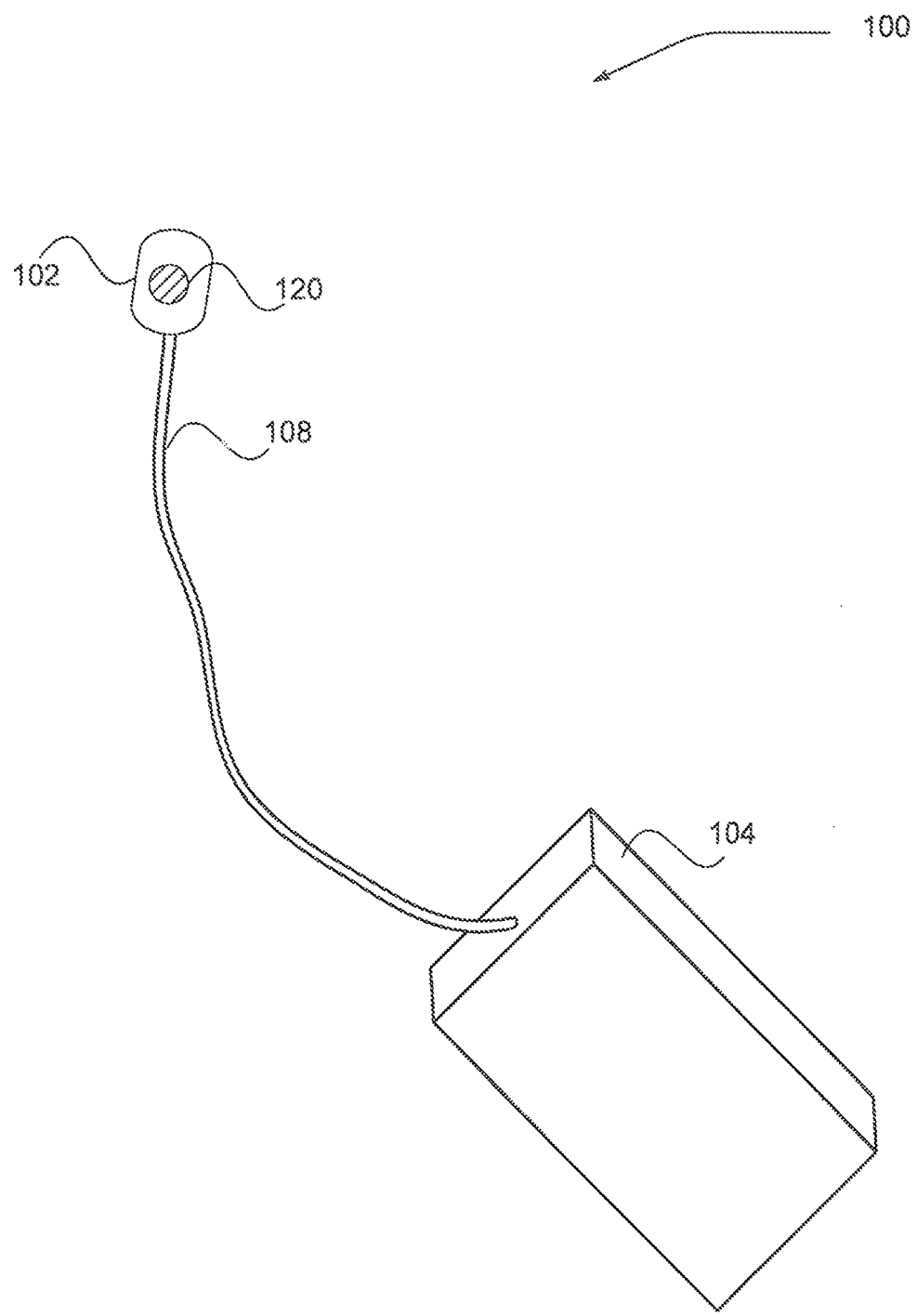
FIG. 1 shows one embodiment of a stimulation system having an electrode lead body and a stimulation unit.

The invention now will be described more fully hereinafter with reference to the accompanying drawings, which form a part hereof, and which show, by may of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled, in the art. Among other things, the invention may be embodied as methods or devices. The following detailed description is, therefore, not to be taken in a limiting sense.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "of" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Briefly stated the invention is directed towards a self anchoring implantable device far stimulating body tissue. The implantable device includes an electrode lead body and at least one stimulating electrode contact disposed on or within the electrode lead body, the lead body being configured and arranged to be self anchoring within body tissue. In addition, the invention is directed to methods of making and using such self anchoring implantable devices.

In one embodiment, the electrode lead body is configured and arranged to be inserted within body tissue. After insertion, rotation of the electrode lead body may be induced about a pivot point of the electrode lead body such that the electrode lead body may become wedged within the surrounding body tissue. In one embodiment, the electrode lead body includes at least one anchoring member that enables the electrode lead body to become anchored within the body tissue. In one embodiment, the at least one anchoring member may include at least one gripping tooth, hook, blade, barb, or the like. The rotation of the electrode lead body may be achieved, in one embodiment, through use of an electrode lead connector (lead wire), or the like, coupled to the electrode lead body and off-center from a pivot point of the electrode lead body. In one embodiment, the electrode lead body may be configured and arranged to include an extraction mechanism to enable removable of the electrode lead body from the body tissue. For example, in one embodiment, the extraction mechanism may include a second wire coupled to the electrode lead body and arranged such that when a determined force, such as a tensional force, is exerted through the second wire, the electrode lead body may rotate about the pivot point to become unanchored, or unwedged, from the body tissue. An additional three may be applied to the second wire to extract the electrode lead body from the body tissue.

Such self anchoring arrangements can also be used to anchor a catheter in place. For example, the catheter can be a part of an implantable drug delivery system. The catheter is typically implanted in the proximity of the tissue to be treated. A catheter typically includes a catheter body surrounding one or more lumens and defining one or more openings near a distal end of the catheter body to allow flow of material into, or out of, a patient.

Implantable sensors can also be anchored using the self anchoring arrangement. Examples of sensors include, but are not limited to, electrical activity sensors (e.g., electroencephalograph, electrocardiograph, electromygraph, and electronystagmograph sensors); chemical sensors (e.g., glucose and drug sensors); and mechanical activity sensors (e.g., pressure, strain, stress, position, velocity, and acceleration sensors.)

These types of implantable devices can also be combined. For example, an electrode lead may also include a catheter lumen to provide drugs or other medications to the tissue to be stimulated or to other proximate tissue. As another example, an electrode lead can include one or more of the sensors described above. Yet another example is a catheter that includes one or more of the above-described sensors.

Thus, while for purposes of illustration, an electrode lead body will be used in the description below, it will be readily apparent that the electrode lead body can be replaced with a micro stimulator, a catheter, a sensor lead, or even a combination of these in the embodiments below, and that the described self anchoring arrangements can be adapted to such devices.

ILLUSTRATIVE EMBODIMENTS

FIG. 1 shows one embodiment of a stimulation system 100 that may be configured to provide electrical stimulation to selected nerves or other body tissue throughout a patient's body. As shown, stimulation system 100 includes an implantable electrode lead body 102, and a lead connector (or lead wire) 108 for use in connection of the electrode contact(s) 120 to a control unit 104. Electrode contact 102 is disposed on the implantable electrode lead body 102 and is coupled to control unit 104 through lead connector 108.

Electrode lead body 102 may be constructed from any of a variety of suitable non-conductive substrate material, including but not limited to, silicone, polyurethane, Silastic™, other plastics, or the like, or combinations thereof, wherein one or more electrode contacts 120 may be placed on or within at least one major surface. Generally, the electrode lead body 102 is made using a hiocompatible material.

Although a single electrode contact 120 is illustrated in FIG. 1, the invention is not so limited. Thus, a plurality of electrode contacts 120 may also be employed. Moreover, the plurality of electrode contacts 120 may be arranged in any of a variety of configurations. For example, if there is more than one electrode contact, the electrode contacts can be spaced in any regular or irregular arrangement. Moreover, in one embodiment, lead connector 108 may be arranged and configured as a branched structure with one or more electrode contacts 120 associated with each branch.

The electrode contact(s) 120 may be made of any of a variety of suitable biocompatible conductive material, such as metal, graphite, conductive oxide, or the like. Examples of other suitable materials include platinum, iridium, platinum iridium alloy, stainless steel, titanium, or tungsten. Any type of electrode contact 120 can be used including monopolar electrodes, bipolar electrode contacts, and other multipolar electrode contacts. A variety of shapes can be used for the electrode contact(s) 120 including, for example, rings around the electrode lead body 102 in the form of circles, ovals, partial rings, squares, rectangles, triangles, or the like, disposed on or within an electrode lead body 102. Other electrode contact configurations can be used as well.

In some embodiments, two or more different types of electrode contact(s) 120 can be provided including, for example, recording electrode contacts and stimulation electrode contacts. Examples of deep brain stimulation leads that include electrode contacts are provided in U.S. patent application Ser. Nos. 11/030,546; 11/230,052; 11/120,526; 11/237,159; and 11/241,156, each of which is incorporated herein by reference. Recording electrode contacts can be used, for example, to monitor insertion of the paddle or lead and determine where the tissue to be stimulated is located. Subsequently, the stimulation electrode contacts 120 can be used to stimulate the tissue. In some embodiments, the stimulation electrode contacts can also function as recording electrode contacts.

Examples of suitable control units 104 and lead connectors 108 include those described in U.S. Pat. Nos. 6,516,227, 6,609,029, and 6,741,892, each of which are incorporated herein by reference, as well as the Precision™ Spinal Cord Stimulation System available from Boston Scientific Neuromodulation, Corporation, Valencia, Calif., and/or other commercially available stimulator units.

It will be recognized that this embodiment (as well as all other embodiments of an electrode lead body illustrated in the Figures) can be modified for use as a micro stimulator, a catheter with one or more openings at or near a distal end, or a sensor with one or more sensor electrodes instead of lead electrode contacts.

Thus, for example, electrode lead body 102 may be modified for use with a microstimulator. Examples of such micro stimulators are described in U.S. Pat. Nos. 5,193,539; 5,193,540; 5,312,439; and 6,051,017; U.S. Patent Application Publication No. 2004/059392; U.S. patent application Ser. Nos. 11/040,209; 11/056,762; 11/084,368; and 11/238,240 and PCT Patent Applications Publication Nos. 98/37926; 98/43700; and 98/43701, all of which are incorporated herein by reference. The BION™ micro stimulator, available from Boston Scientific Neuromodulation, Corporation, Valencia, Calif., is an example of a micro stimulator.

Electrode lead body 102 may also be modified for use with an implantable electrode paddle. Examples of implantable electrode paddles are provided in U.S. patent application Ser. Nos. 11/376,360; 11/319,291; and 11/396,309, each of which is incorporated herein by reference. However, the invention is not constrained to electrode paddles. For example, electrode cuff or electrode lead arrangements may also be employed. Examples of implantable electrode cuffs are provided in U.S. patent application Ser. Nos. 11/393,991, and 11/294,283, each of which is incorporated herein by reference.

In one embodiment, a method of using stimulation system 100 includes implanting the electrode lead body 102 into a patient's tissue in proximity to the tissue to be stimulated. An electrical signal may be provided by control unit 104 through lead connector 108 to electrode contact 120 to stimulate the tissue. At least a portion of stimulation system 100 can be implanted into the body tissue using a variety of methods including surgical methods. In one embodiment, control unit 104 may remain external to the patient's body. In another embodiment, control unit 104 may also be located within the patient's body.

Where there are more than one electrode contact(s) 120, they may be selectively stimulated by control unit 104. Electrical signals may be provided to the electrode contacts 120 of the stimulator simultaneously. Alternatively, electrical signals can be provided to the electrode contacts 120 independently of one another. Coordination of the electrical signals provided to the electrode contact(s) 120 may be facilitated by control writ 104.

Control unit 104 may be used to provide various electrical signals to the electrode contact(s) 120 to stimulate nerve, fiber, or other body tissue, including, but not limited to prepulsing stimulations, or other waveform stimulations. In one embodiment, the electrical signals may be applied to provide a hybrid of depth stimulations. In another embodiment, the electrical signals may be applied on different timing channels to the electrode contact(s) 120.

Figure 2A:
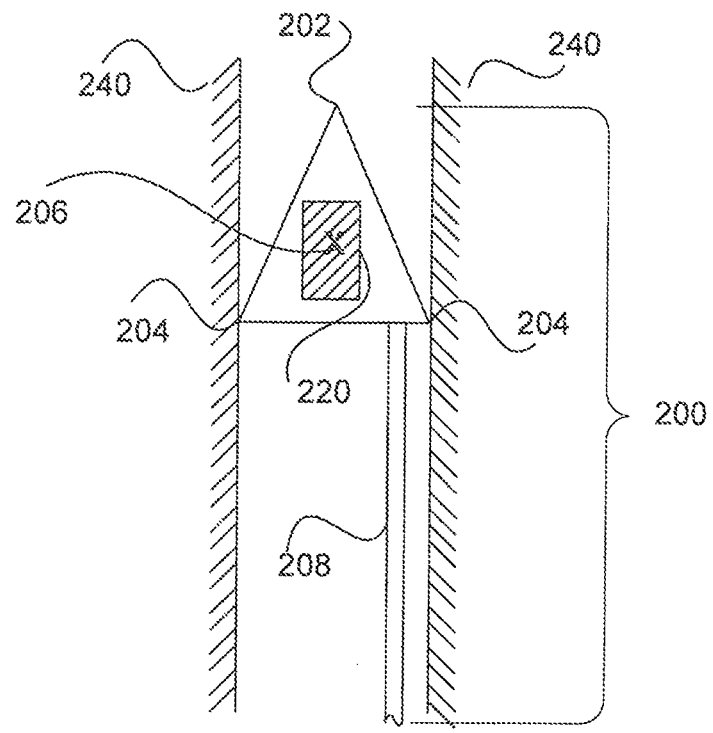
FIGS. 2A-2B show schematic side views of one embodiment of a self anchoring electrode lead system.
Figure 2B:
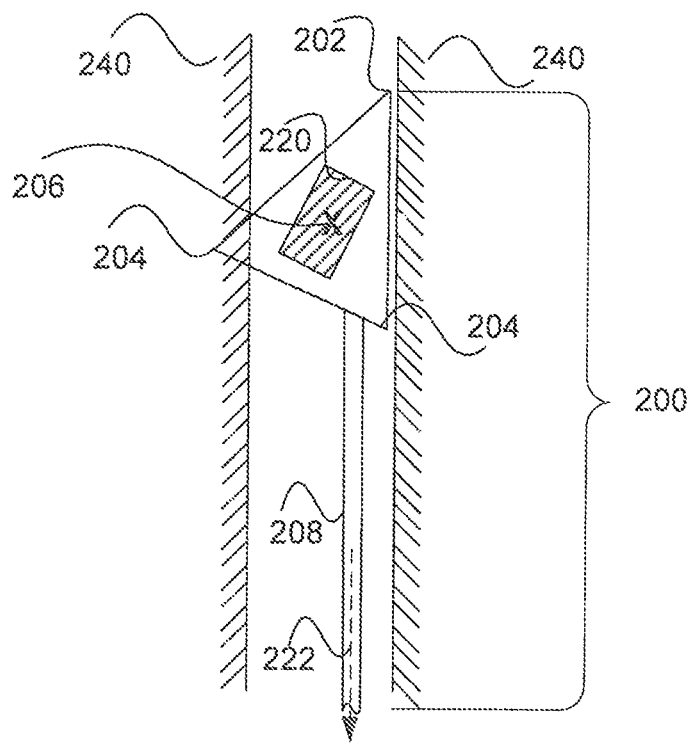

FIGS. 2A-2B show schematic side views of one embodiment of a self anchoring electrode system 200. As shown, self anchoring electrode system 200 includes electrode lead body 202, at least one electrode contact(s) 220, and lead connector 208. Lead connector 208 is illustrated as being coupled to electrode lead body 202 off center from a pivot point 206 about which electrode lead body 202 may be configured to rotate. Lead connector 208 may be similar to lead connector 108 of FIG. 1. Electrode contact(s) 220 may be similar to electrode contact 120 of 10 FIG. 1.

As shown in FIGS. 2A-2B, electrode lead body 202 may be implanted within body tissue 240, implantation of electrode lead body 202 may be performed using a variety of techniques. For example, in one method of implanting the electrode lead body 202, access to the desired position in a patient's body can be accomplished by opening a hole through the patient's skin. The point of entry, as well as whether a hole may be made in other tissues prior to inserting the electrode lead body 202, will depend on the application. The electrode lead body 202 can be inserted into the tissue and guided to the target location within the body. An optional recording electrode(s) can be observed using an external control unit to identify the target tissue, if desired. In one embodiment, an insertion tool may be employed to enable implantation of electrode lead body 202 into the patient's body. Examples of implantable electrode insertion tools, are described in U.S. patent application Ser. No. 11/124,843, and U.S. Pat. No. 7,033,326, each of which is incorporated herein by reference.

FIG. 2B illustrates that when a tensional force 222 is exerted through lead connector 208, electrode lead body 202 may rotate about pivot point 206 such that at least one edge 204 of electrode lead body 202 becomes wedged into body tissue 240, such that the electrode lead body 202 is anchored and restrained from migration, in one embodiment, at least a portion of edge 204 may be sharp, such that it may cut at least some of the body tissue 240 as electrode lead body 202 is rotated.

Although electrode lead body 202 is illustrated as approximately triangular in shape, the invention is not so constrained, and other shapes may be employed that include at least one edge 204 for anchoring electrode lead body 202 to the surrounding body tissue. Thus, for example, electrode lead body 202 may be rectangular, square, oval, oblong, rhomboidal, pyramidoidal, tetrahedraic, cubic, or the like.

In one embodiment, a material may be injected through lead connector 208 after implantation. The injected material can be, for example, a material that encourages sear tissue formation to promote anchoring of electrode lead body 202 to the surrounding body tissue 240. In another embodiment, a chemical coating may be applied to at least one edge 204 to facilitate sear tissue formation and enhance the anchoring of the electrode lead body 202.

Figure 3:
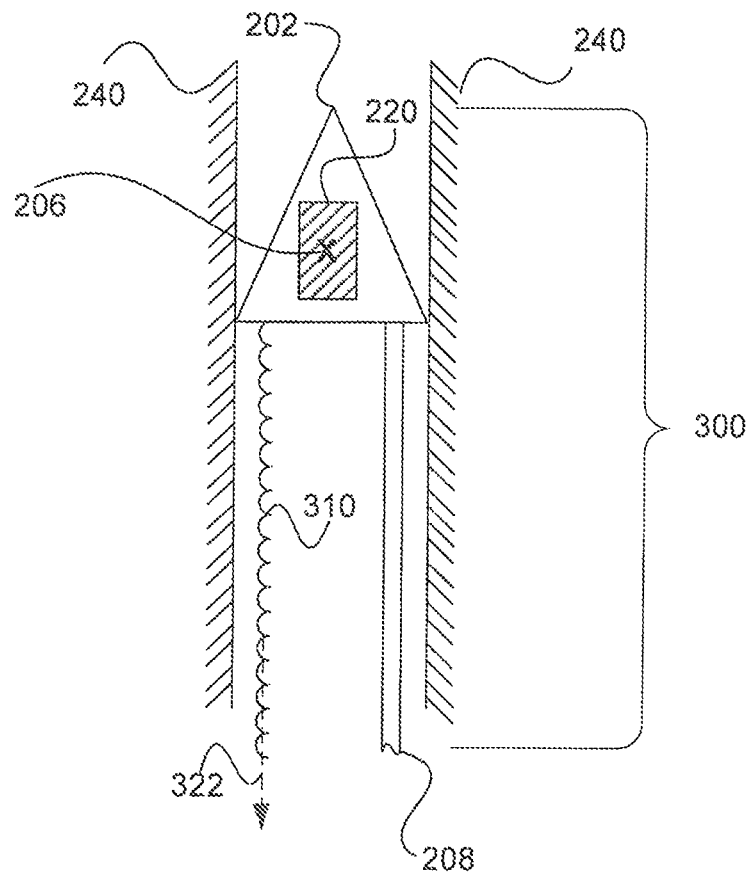
FIG. 3 shows a schematic side view of another embodiment of a self anchoring electrode lead system having an extraction mechanism.

FIG. 3 shows a schematic side view of another embodiment of a self anchoring electrode system 300 having a mechanism for extraction. As seen in the figure, an extraction mechanism, such as wire 310 may be coupled to electrode lead body 202 in an opposing fulcrum position to lead connector 208, and off centered from pivot point 206. In one embodiment, wire 310 may be made of a flexible material, such as a biocompatible cord, string, plastic, wire, or the like.

During extraction, a force 322 is applied through wire 310 causing electrode lead body 202 to rotate about the pivot point 206 into an insertion orientation, such that edge(s) 204 become dislodged from the surrounding body tissue 240. Self anchoring electrode system 300 may then be extracted from the patient's body. In one embodiment, extraction from the patient's body may be achieved by pulling on both wire 310 and lead connector 208. In one embodiment, a cross section of wire 310, and lead connector 208 may be selected to be approximately equal to a cross sectional profile of electrode lead body 202, allowing electrode lead body 202 to be extracted along a preserved encapsulated extraction path within the body tissue.

Figure 4A:
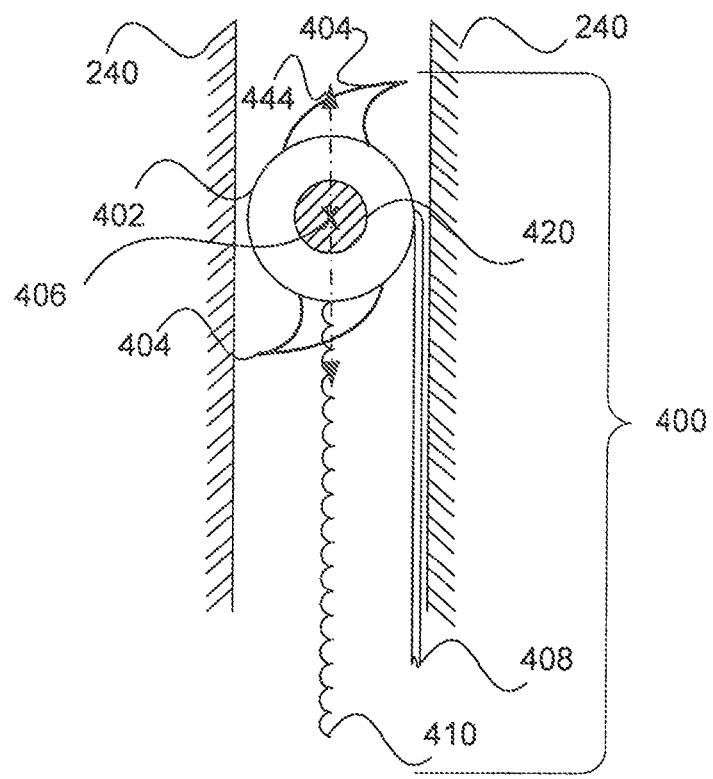
FIGS. 4A-4B show schematic side views of still another embodiment of a self anchoring electrode lead system, according to the invention.
Figure 4B:
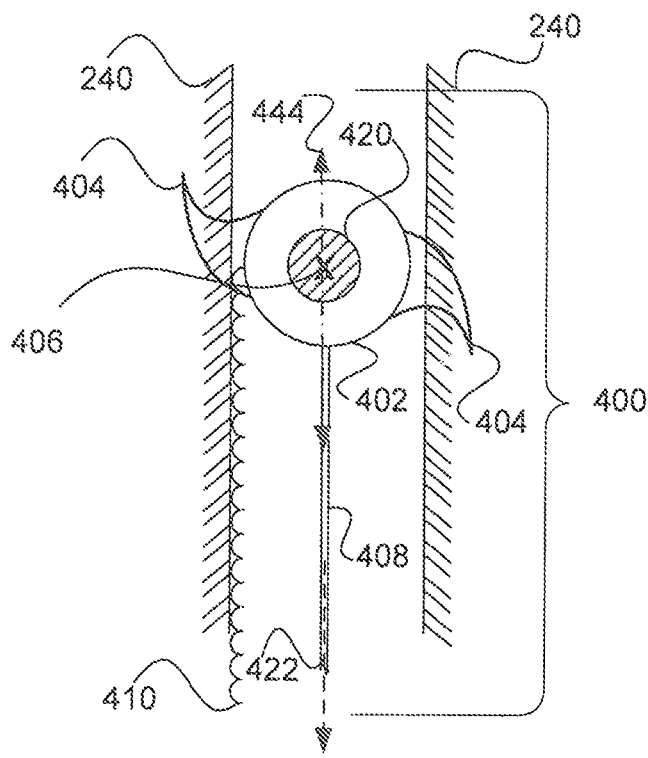

FIGS. 4A-4B show schematic side views of still another embodiment of a self anchoring electrode lead system. As shown in the figure, self anchoring electrode lead system 400 includes electrode lead body 402 that has a lead connector 408 for use in connection of the electrode contact(s) 420 to a control unit, such as control unit 104 of FIG. 1. Lead connector 408 may be similar to lead connector 108 of FIG. 1. Electrode contact(s) 420 may be similar to electrode contact 120 of FIG. 1.

Electrode lead body 402 is illustrated as approximately spherical in shape; however, other shape may also be employed. For example, electrode lead body 402 may also be oval, or even spherical in shape.

Coupled to electrode lead body 402 are one or more anchoring members 404, such as, for example, teeth, spikes, barbs, or the like, that are configured to provide anchoring of the self anchoring lead system 400 into the surrounding body tissue 240.

The anchoring members 404 may be arranged and configured such that when the electrode lead body 402 is positioned within the body tissue 240 in a first position, as shown FIG. 4A, the electrode lead body 402 may be readily implanted or extracted from the body tissue 240. In one embodiment, the anchoring members 404 may be arranged around electrode lead body 402 to be approximately in line with implantation/extraction axis line 444.

The lead connector 408 may be coupled to the electrode lead body 402 such that when a force 422 is applied, electrode lead body 402 rotates about a pivot point 406 to a second position, such that the anchoring members 404 become wedged or locked into the body tissue 240 to resist migration of the self anchoring lead system 400, such as shown in FIG. 4B. Thus, in one embodiment, lead connector 408 may be coupled to the electrode lead body 402 at a juncture approximately perpendicular to the implantation/extraction axis line 444.

Coupled to the electrode lead body 402 may also be an optional extraction wire 410 that is configured and arranged such that when a force is applied to the extraction wire 410, electrode lead body 402 rotates about the pivot point 406 back to the first position, as shown in FIG. 4A, enabling ready removal of the self anchoring lead system 400 from a patient's body. For example, in one embodiment, extraction wire 410 may be coupled to the electrode lead body 402 approximately in line with implantation/extraction axis line 444, and further, at a position towards an extraction path for the electrode lead body 402. In one embodiment, extraction wire 410 may be configured from a flexible, biocompatible material, including, string, metal, plastic, or the like.

In at least one embodiment, the anchoring members 404 may have a spring-like quality that results in the expansion of the members when a force is applied to lead connector 408. For example, the authoring members 404 can be made of thin strips of resilient metal or plastic or a compressible bladder. When more than one anchoring members 404 is provided, the anchoring members 404 can be distributed in a regular or irregular pattern around the electrode lead body 402.

In some embodiments, the end of the anchoring members 404 is made using a rigid material, such as stainless steel or another metal, to anchor in the body tissue 240, but the remainder of the anchoring members 404 can be made of a flexible material, such as Silastic™, or other plastic material, to facilitate implantation.

The above specification, examples, and data provide a description of the manufacture and use of the composition of the invention. Since many embodiments of the invention can be made without departing from the spirit and scope of the invention, the invention also resides in the claims hereinafter appended.

What is claimed and desired to be protected under United States Letters Patent:

1. An implantable device for use in stimulating body tissue, comprising:
    a body comprising at least one stimulating electrode contact disposed on the body, the body defining a center of the body and at least one anchoring member;
    a lead connector coupled to the body and extending from the body; and
    wherein the implantable device is configured and arranged such that when the implantable device is implanted in body tissue and a force is applied to pull the lead connector, the body is rotated about the center of the body such that the at least one anchoring member impinges on the body tissue to anchor the implantable device within the body tissue.

2. The implantable device of claim 1, wherein the lead connector comprises a wire electrically coupled to the at least one stimulating electrode contact.

3. The implantable device of claim 1, wherein the anchoring member comprises at least one edge of the body.

4. The implantable device of claim 3, wherein the body is triangular with three corners and the anchoring member comprises at least one of the corners.

5. The implantable device of claim 1 wherein the anchoring member comprises at least one of a tooth, a barb, a hook, or a blade.

6. The implantable device of claim 1, wherein the body comprises a circular core and the anchoring member extends from the circular core.

7. The implantable device of claim 6, wherein the anchoring member comprises at least one of a tooth, a barb, a hook, or a blade.

8. The implantable device of claim 6, wherein the anchoring member comprises at least two anchoring elements, each anchoring element comprising al least one of a tooth, a barb, a hook, or a blade.

9. The implantable device of claim 8, wherein the at least two anchoring elements comprise two anchoring elements extending from the circular core opposite each other.

10. The implantable device of claim 1, further comprising a stimulation control unit coupleable to the at least one electrode contact through the lead connector and configured and arranged to enable electrical stimulation of the body tissue.

11. The implantable device of claim 1, further comprising an extraction wire coupled to the body, wherein the extraction wire is configured and arranged such that when a sufficient force is applied through the extraction wire the body is rotated to dislodge the anchoring member from the body tissue.

12. The implantable device of claim 11, wherein the extraction wire further comprises a biocompatible, flexible material.

13. The implantable device of claim 1, wherein the anchoring member further comprises a chemical coating configured and arranged to adhere to the body tissue or to cause scar tissue formation.

14. The implantable device of claim 1, wherein the lead connector is configured and arranged to permit scar tissue formation material to be injected through the lead connector to a position of the body.

15. A method of implanting an implantable device into a patient, the method comprising:
    implanting the implantable device of claim 1 into a patient; and pulling on the lead connector to rotate the body of the implantable device about the center of the body to impinge on body tissue of the patient to anchor the implantable device within the patient.

16. The method of claim 15, wherein the implantable device further comprises an extraction wire coupled to the body;

wherein the method further comprises pulling the extraction wire causing the body of the implantable device to rotate about the center of the body to dislodge the anchoring member from the body tissue.

17. The method of claim 15, further comprising injecting scar tissue formation material through the lead connector to a position of the body of the implantable device.

18. The method of claim 15, wherein pulling on the lead connector comprises pulling on the lead connector to rotate the body of the implantable device so that a corner of the body impinges on the body tissue of the patient to anchor the implantable device within the patient.

19. The method of claim 15, wherein the anchoring member comprises at least one anchoring element selected from a tooth, a barb, a hook, or a blade;

wherein pulling on the lead connector comprises pulling on the lead connector to rotate the body of the implantable device so that the at least one anchoring element impinges on the body tissue of the patient to anchor the implantable device within the patient.

20. The method of claim 15, further comprising coupling the implantable device to a stimulation control unit configured to enable electrical stimulation of the body tissue using the at least one stimulating electrode contact.

\* \* \* \* \*